(12) United States Patent
Janssen et al.

(10) Patent No.: US 8,053,243 B2
(45) Date of Patent: Nov. 8, 2011

(54) DETECTION OF NITROSYLATED PROTEINS

(75) Inventors: Yvonne M. Janssen, Charlotte, VT (US); Albert van der Vliet, Essex Junction, VT (US); Karina Ckless, Essex Junction, VT (US); Niki Reynaert, Burlington, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 861 days.

(21) Appl. No.: 11/104,387

(22) Filed: Apr. 12, 2005

(65) Prior Publication Data
US 2005/0238734 A1 Oct. 27, 2005

Related U.S. Application Data

(60) Provisional application No. 60/561,439, filed on Apr. 12, 2004.

(51) Int. Cl.
*G01N 33/00* (2006.01)
(52) U.S. Cl. ......... 436/106; 436/86; 436/107; 436/110; 436/119; 436/172; 436/538; 435/188; 435/194; 435/375; 435/7.5; 204/461; 424/718
(58) Field of Classification Search .................. 422/61; 436/56, 86, 538, 106, 107, 110, 119, 172; 435/188, 194, 375, 6, 7.5; 204/461; 424/718
See application file for complete search history.

(56) References Cited

U.S. PATENT DOCUMENTS
5,851,812 A * 12/1998 Goeddel et al. ............... 435/194
(Continued)

FOREIGN PATENT DOCUMENTS
WO WO 02/39119 5/2002
(Continued)

OTHER PUBLICATIONS

Martin Spiecker, "Differential regulation of endothelial cell adhesion molecule expression by nitric oxide donors and antioxidants", Jun. 1998, Journal of Leukocyte Biology, vol. 63, pp. 732-739.*

(Continued)

*Primary Examiner* — In Suk Bullock
*Assistant Examiner* — Dennis M White
(74) *Attorney, Agent, or Firm* — Wolf, Greenfield & Sacks, P.C.

(57) ABSTRACT

The present invention, in some aspects, relates to systems and methods for determining oxidized proteins, including nitrosylated proteins such as S-nitrosylated proteins. The systems and methods of the invention can be used in vitro (e.g., in cell or tissue culture) or in vivo. For instance, in some cases, the invention can be used to spatially determine the location and/or concentration of oxidized proteins within cells and/or tissues (e.g., through visual detection). In one set of embodiments, a nitrosylated or otherwise oxidized moiety on a protein may be reacted with a detection entity, which may be, for example, fluorescent, radioactive, electron-dense, able to bind to a signaling entity or a binding partner in order to produce a signal, etc. In some embodiments, other moieties on the protein may be altered or blocked before reaction of the protein with the detection entity. Such moieties on the protein may be, for instance, non-oxidized or non-nitrosylated moieties able to react with the detection entity. Also provided in certain aspects of the present invention are kits for determining oxidized proteins, which may include components such as detection entities, alkylating agents, blocking agents, reducing agents, signaling entities, binding partners, antibodies, instructions, and the like.

8 Claims, 9 Drawing Sheets

U.S. PATENT DOCUMENTS

| | | | |
|---|---|---|---|
| 6,806,057 B2 | 10/2004 | Snyder et al. | |
| 7,001,738 B2 | 2/2006 | Snyder et al. | |
| 2002/0102744 A1* | 8/2002 | Snyder et al. | 436/538 |
| 2005/0026227 A1 | 2/2005 | Snyder et al. | |

FOREIGN PATENT DOCUMENTS

| | | |
|---|---|---|
| WO | WO 02/42773 | 5/2002 |

OTHER PUBLICATIONS

Gow et al,"Basal and stimulated protein S-Nitrosylation in multiple cell types and tissues", Mar. 22, 2002, JBC, vol. 277, 12, pp. 9637-9640.*

Li et al, "Regulation of protein tyrosine phosphatase 1B in intact cells by S-nitrosothiols", Feb. 15, 2003, Arch Biochem Biophys, 410(2):269-79.*

Seligman et al, "Protein thiols in spermatozoa and epidiymal fluid of rats" 1991, J. Reprod. Pert. vol. 93, pp. 399-408.*

Gainer et al, "Histochemical Demonstration of Thiols and Disulfides by the Fluorescent Labeling Agent, Monobromobimane: An Application to the Hypothalamo-Neurohypophysial System", Histochemistry, 1980, vol. 68, p. 309-315.*

Ceccatelli et al, "Nitric oxide synthase in the rat anterior pituitary gland and the role of nitric oxide in regulation of luteinizing hormone secretion" Proc. Natl. Acad. Sci. vol. 90, Dec. 1993, p. 11293, Fig. 1.*

Xian et al, "Inhibition of Papain by S-Nitrosothiols" Journal of Biological Chemistry, vol. 275, No. 27, Jul. 7, 2000, p. 20467-20473, Scheme 1 on page 20470.*

Ckless, Karina et al., "In situ detection and visualization of S-nitosylated proteins following chemical derivatization: identification of Ran GTPase as a target for S-nitosylation," NITRIC OXIDE Biology and Chemistry, 11, (2004), pp. 216-227.

Ckless, Karina et al., Abstract # 214, "Detection of Nuclear S-Nitrosation in Lung Epithelial Cells Using Chemical Derivitization and Immunocytochemistry," Supplement to FREE RADICAL BIOLOGY & MEDICINE, The Official Journal of the Oxygen Society, A Constituent Member of the International Society for Free Radical Research, 9$^{th}$ Annual Meeting of The Oxygen Society, Program Abstracts, Nov. 20-24, 2002, San Antonio Marriott Rivercenter, San Antonio, TX, USA, vol. 33, Supplement 2, 2002.

Ckless, Karina et al., Abstract # 246, "Increased NO Production, By Arginase Inhibition, Modulates IKB Kinase Activity," Supplement to FREE RADICAL BIOLOGY & MEDICINE, The Official Journal of The Oxygen Society, An Affiliate Journal of the International Society for Free Radical Research, SFRBM's 10$^{th}$ Annual Meeting, Program Abstracts, Nov. 20-24, 2003, Sheraton Hotel & Towers, Seattle, WA, USA, vol. 33, Supplement 1, 2003.

Jaffrey, Samie R., "Protein S-nitrosylation: a physiological signal for neuronal nitric oxide," NATURE CELL BIOLOGY, vol. 3, Feb. 2001, pp. 193-197.

Molecular Probes Invitrogen detection technologies, §2.1, "Introduction to Thiol Modification and Detection," http://probes.introgen.com/handbook/sections/0201.html Updated: Dec. 5, 2004.

Reynaert, Niki L., "Nitric oxide represses inhibitory κB kinase through S-nitosylation," Proc. Natl. Acad. Sci. USA, Jun. 15, 2004, vol. 101, No. 24, pp. 8945-8950.

Stuchbury, Trevor et al., "A Reporter Group Delivery System with Both Absolute and Selective Specificity for Thiol Groups and an Improved Fluorescent Probe Containing the 7-Nitrobenzo-2-oxa-1,3-diazole Moiety," Biochem. J., Nov. 1975, vol. 151(2), pp. 417-432.

Yang, Yi et al., "S-nitrosoprotein formation and localization in endothelial cells," Proc. Natl. Acad. Sci. USA, Jan. 4, 2005, vol. 102, No. 1, pp. 117-122.

International Preliminary Report on Patentability, International Application No. PCT/US2005/012259, issued on Oct. 26, 2006.

Bayer, E. A., et al., "Selective Labeling of Sulfhydryls and Disulfides on Blot Transfers Using Avidin-Biotin Technology: Studies on Purified Proteins and Erythrocyte Membranes," Analytical Biochemistry, vol. 161, No. 2, pp. 262-271 (1987).

Garrison, M.D., et al., "Postadsorption Changes in the Emission Maximum of Acrylodan-Labeled Bovine Serum Albumin Using Total Internal Reflection Fluorescence," Journal of Colloid and Interface Science, vol. 148, No. 2, pp. 415-424 (1992).

Jaffrey, S.R., et al., "The Biotin Switch Method for the Detection of S-Nitrosylated Proteins," Science's STKE (Electronic Resource): Signal Transduction Knowledge Environment, No. 86, PL. 1, pp. 1-9 (2001).

Janiszewski, M., et al., "Inhibition of Vascular NADH/NADPH Oxidase Activity by Thiol Reagents: Lack of Correlation with Cellular Glutathione Redox Status," Free Radical Biology & Medicine, vol. 29, No. 9, pp. 889-899 (2000).

Jones, J.G., et al., "Essential and Nonessential Thiols of Yeast Hexokinase. Reactions with Iodoacetate and Iodoacetamide," Biochemistry, vol. 14, No. 11, pp. 2396-2403 (1975).

Reynaert, N. L., et al., "Nitric Oxide and Redox Signaling in Allergic Airway Inflammation," Antioxidants & Redox Signaling, vol. 7, No. 1 & 2, pp. 129-143 (2005).

Scouten, W. H., "N-Dansylaziridine: A New Fluorescent Modification for Cysteine Thiols," Biochimica et Biophysica Acta, vol. 336, No. 2, pp. 421-426 (1974).

Stein, M. J., et al., "Inhibition Ficin by the Chloromethyl Ketone Derivatives of N-Tosyl-L-Lysine and N-Tosyl-L-Phenylalanine," Biochemical and Biophysical Research Communications, vol. 26, No. 3, pp. 376-382 (1967).

Wong, P. S., et al., "Reaction of Organic Nitrate Esters and S-Nitrosothiols with Reduced Flavins: A Possible Mechanism of Bioactivation," Drug Metabolism and Disposition, vol. 27, No. 4, pp. 502-509 (1999).

Wu, H.H., et al., "Pyrrolidine Dithiocarbamate Prevents p53 Activation and Promotes p53 Cysteine Residue Oxidation," The Journal of Biological Chemistry, vol. 273, No. 30, pp. 18898-18905 (1998).

Xian, M., et al., "S-Nitrosothiols as Novel, Reversible Inhibitors of Human Rhinovirus 3C Protease," Bioorganic & Medical Chemistry Letters, vol. 10, No. 18, pp. 2097-2100 (2000).

International Search Report for International Application No. PCT/US05/012259 filed Dec. 12, 2005.

Written Opinion for International Application No. PCT/US05/012259 filed Dec. 12, 2005.

Reynaert, N. L., et al., "In situ detection of S-glutathionylated proteins following glutaredoxin-1 catalyzed cysteine derivatization," Biochimica et Biophysica Acta, 1760, pp. 380-387 (2006).

* cited by examiner

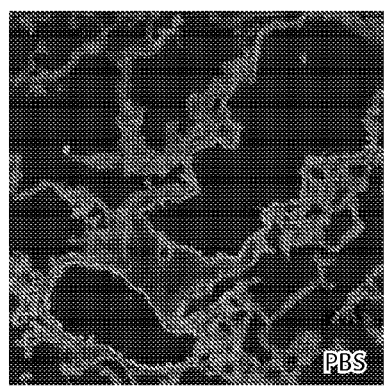
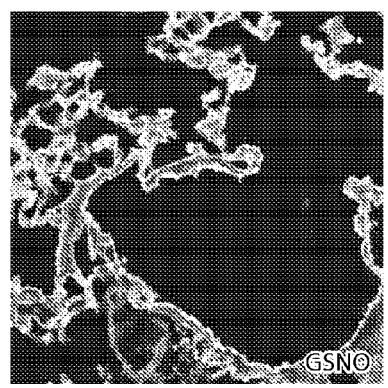
Fig. 5A　　　　　　　　Fig. 5B
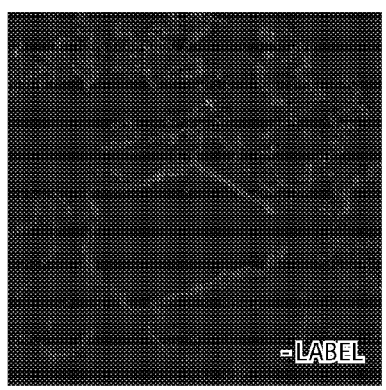
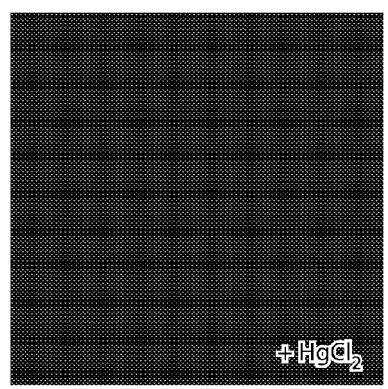
Fig. 5C　　　　　　　　Fig. 5D

DETECTION OF NITROSYLATED PROTEINS

RELATED APPLICATIONS

This application claims the benefit of U.S. Provisional Patent Application Ser. No. 60/561,439, filed Apr. 12, 2004, entitled "Detection of Nitrosylated Proteins," by Janssen, et al., incorporated herein by reference.

FEDERALLY SPONSORED RESEARCH

The present invention was sponsored by the National Institutes of Health, Grant Nos. RO1 HL60014, RO1 HL60812, Public Health Service P20 RL15557 (NCRR COBRE), and PO1 HL67004. The Government may have certain rights in the invention.

FIELD OF INVENTION

The present invention generally relates to systems and methods for determining oxidized proteins, and in particular, to systems and methods for determining nitrosylated proteins. In some cases, the present invention relates to visualization techniques for determining the spatial locations and/or concentrations of nitrosylated or otherwise oxidized proteins within cells and/or tissues.

BACKGROUND

Nitric oxide (NO) is an important mediator in biological systems, playing significant roles in physiology and pathophysiology. For instance, cellular responses to NO are often transduced via multiple chemical reactions, including direct reactions with heme centers and metalloproteins, as well as indirect reactions, including oxidative and other metabolic reactions with various reactive nitrogen species. In particular, reactions of certain reactive nitrogen species with cysteine thiols on proteins that result in nitrosylation of the protein may represent an important post-translational modification capable of transducing certain NO-dependent signals.

Many proteins have been characterized as being targets for S-nitrosylation reactions, including metabolic proteins, structural proteins, cytoskeletal proteins, ion channels, and signaling proteins. In many cases, S-nitrosylation is believed to regulate protein activity and function. For example, S-nitrosylation has been shown to inhibit the activity of caspases, and denitrosylation is often required for the enzymatic activity of these enzymes. Similarly, the S-nitrosylation of p50, which is a subunit of transcription effector nuclear factor kappa B (NF-κB), is believed to be responsible for the NO-induced inhibition of DNA binding activity of transcription factor NF-κB.

Many of the proteins targeted by S-nitrosylation were originally identified using exogenous NO donors, and it has not always been established whether S-nitrosylation of these proteins is associated with endogenous NO activity. This is primarily due to limitations in the methodology typically used to detect S-nitrosylated proteins.

SUMMARY OF INVENTION

The present invention generally relates to systems and methods for determining oxidized proteins, such as nitrosylated proteins. In some cases, the present invention relates to visualization techniques for spatially determining the spatial locations and/or concentrations of nitrosylated or otherwise oxidized proteins within cells and/or tissues. The subject matter of the present invention involves, in some cases, interrelated products, alternative solutions to a particular problem, and/or a plurality of different uses of one or more systems and/or articles.

One aspect of the invention provides a method for determining protein nitrosylation. The method, in one set of embodiments, includes the steps of reacting a first thiol moiety on a protein to form an alkylthio moiety, reacting a nitrosothiol moiety on the protein to form a second thiol moiety, and reacting the second thiol moiety with an alkylating agent comprising a detection entity to form a second alkylthio moiety to determine protein nitrosylation.

In another set of embodiments, the method is defined, at least in part, by a step of reacting a nitrosothiol moiety on a protein to form an alkylthio moiety. In yet another set of embodiments, the method includes the steps of reacting a first thiol moiety on a protein to form an alkylthio moiety, and reacting a nitrosothiol moiety on the protein to form a second thiol moiety.

In one set of embodiments, the method comprises a step of spatially determining a nitrosylated protein in tissue. In still another set of embodiments, the method includes a step of non-reversibly reacting a nitrosothiol moiety on a protein with a detection entity.

The method, in one set of embodiments, includes a step of applying an inhibitor to inhibitory kappa B kinase (IKK) to reduce activity of nuclear factor kappa B (NF-κB). In some cases, the inhibitor comprises NO. In one embodiment, the inhibitor is applied to the beta subunit of inhibitory kappa B kinase (IKKβ). In another set of embodiments, the method includes a step of applying a promoter to inhibitory kappa B kinase to increase activity of nuclear factor kappa B.

A kit is provided in another aspect of the invention. In certain embodiments, the kit includes a container housing an alkylating agent and a reducing agent. In some cases, the alkylating agent is able to react a first thiol moiety on a protein to an alkylthio moiety, and the reducing agent is able to react a nitrosothiol moiety on the protein to a second thiol moiety.

In another aspect, the present invention is directed to a method of promoting one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures:

FIGS. 5A-5D are photomicrographs of frozen lung sections demonstrating the detection of S-nitrosylated proteins in a tissue, according to another embodiment of the invention;

DETAILED DESCRIPTION

Figure 1:
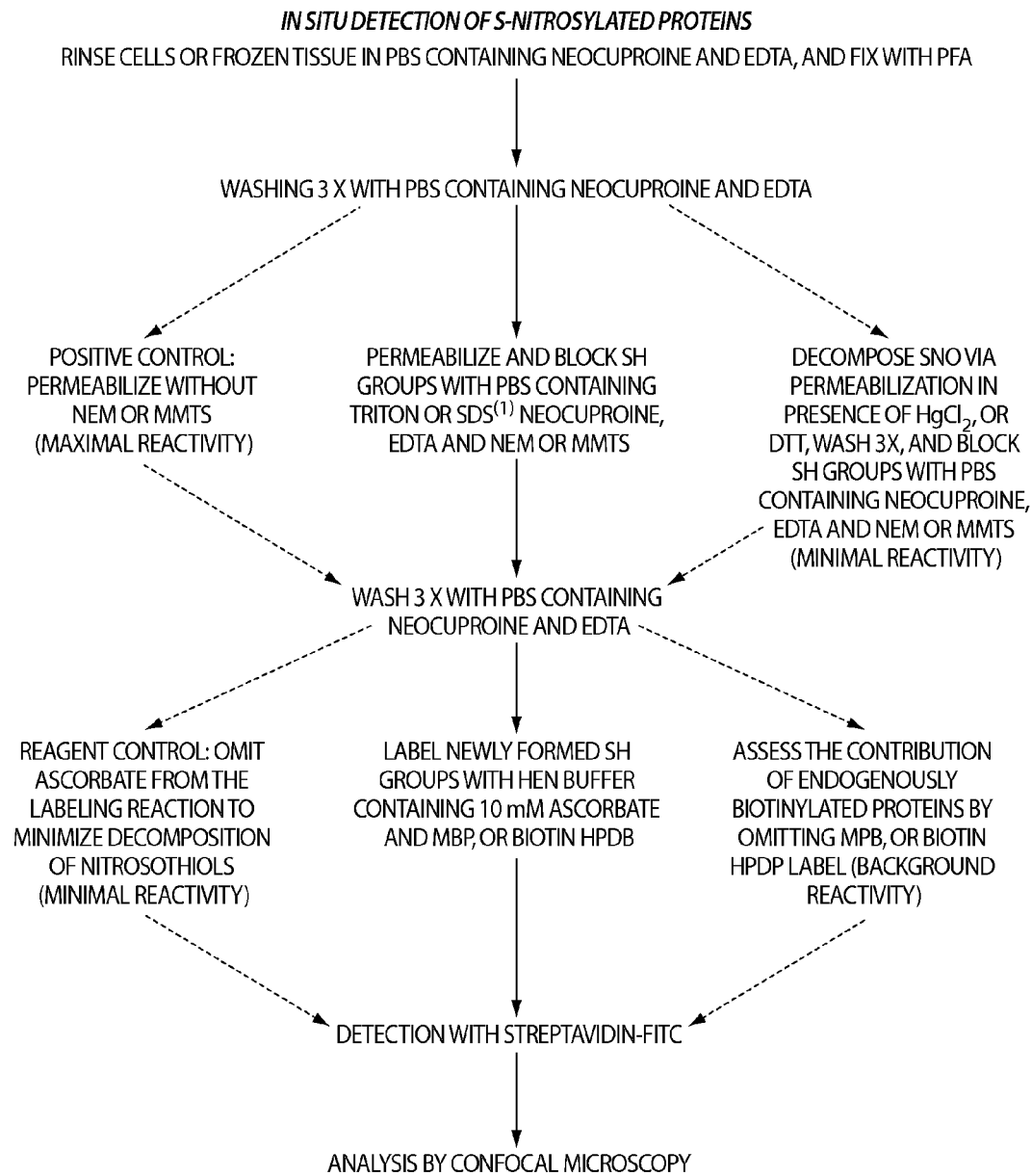
FIG. 1 is a schematic diagram of a procedure for determining S-nitrosylated proteins in situ, according to one embodiment of the invention.

The present invention, in some aspects, relates to systems and methods for determining oxidized proteins, including nitrosylated proteins such as S-nitrosylated proteins. The systems and methods of the invention can be used in vitro (e.g., in cell or tissue culture) or in vivo. For instance, in some cases, the invention can be used to spatially determine the location and/or concentration of oxidized proteins within cells and/or tissues (e.g., through visual detection). In one set of embodiments, a nitrosylated or otherwise oxidized moiety on a protein may be reacted with a detection entity, which may be, for example, fluorescent, radioactive, electron-dense, able to bind to a signaling entity or a binding partner in order to produce a signal, etc. As a specific example, a nitrosothiol moiety on a nitrosylated protein may be reacted with an alkylating agent to form an alkylthio moiety; the alkylthio moiety may include a detection entity or otherwise be able to interact with a signaling entity. In some embodiments, other moieties on the protein may be altered or blocked before reaction of the protein with the detection entity. Such moieties on the protein may be, for instance, non-oxidized or non-nitrosylated moieties able to react with the detection entity. As a particular example, in a protein containing nitrosothiol and (non-nitrosylated) thiol moieties, the thiol moieties may first be altered or blocked prior to reaction of the protein with the detection entity. Also provided in certain aspects of the present invention are kits for determining oxidized proteins, which may include components such as detection entities, alkylating agents, blocking agents, reducing agents, signaling entities, binding partners, antibodies, instructions, and the like.

Various aspects of the present invention relate to systems and methods for determining oxidized proteins, including nitrosylated proteins such as S-nitrosylated proteins. In some aspects, the present invention relates to visualization techniques for spatially determining the spatial locations and/or concentrations of nitrosylated or otherwise oxidized proteins within cells and/or tissues. An "oxidized" protein, as used herein, is a protein in which at least one (native) amino acid residue of the protein has been oxidized in some fashion. As one example, a residue on the protein may be a deaminated residue. As another example, a nitrous oxide (NO) compound may react with a residue on the protein to nitrosylate the residue. Thus, as used herein, a "nitrosylated" protein is a protein in which at least one amino acid residue of the protein has been reacted with NO, typically through the addition of NO to the residue. Residues that may undergo nitrosylation include sulfhydryl moieties (—SH) (e.g., from a cysteine residue), hydroxyl moieties (—OH) (e.g., from a serine residue or a threonine residue) (also referred to as "nitration"), or the like. As a particular example, if the residue includes a sulfhydryl moiety (—SH) (also referred to as a thiol moiety), the addition of NO to the residue can produce a nitrosothiol moiety (—S—N=O). Such a reaction can also be referred to herein as an "S-nitrosylation" reaction, where the "S—" signifies reaction with the sulfhydryl moiety.

It should be understood that, in the following descriptions, although the determination of oxidized proteins is often described in terms of the determination of S-nitrosylated proteins, this is by way of example only, and the determination of other types of oxidized proteins and/or nitrosylated proteins is also within the scope of the invention. As used herein, "determining" refers to the detection and/or analysis of an entity, either quantitatively or qualitatively. Determination of an entity may include determination of the presence or absence of the entity, and/or a measurement of the amount or degree of the entity, e.g., the concentration of the entity, the density of the entity, etc. In some cases, the location of an entity may be determined, for example, the location of the entity within a cell, within a tissue, etc.

According to one aspect, an oxidized protein can be determined by attaching a detection entity to an oxidized residue on the protein, for example, the protein may be spatially or visually determined. As used herein, a "detection entity" is an entity that can be determined in some fashion, either directly or indirectly. For instance, the detection entity may be fluorescent, radioactive, electron-dense, a member of a binding pair, a substrate for an enzymatic reaction, an antigen for an antibody, etc. In some cases, the detection entity itself is not directly determined, but instead interacts with a second entity (a "signaling entity") in order to effect determination; for example, coupling of the signaling entity to the detection entity may result in a determinable signal. As examples, the detection entity and the signaling entity may each include one member of a binding pair, for example, nucleic acid/nucleic acid, nucleic acid/protein, protein/protein, antibody/antigen, antibody/hapten, enzyme/substrate, enzyme/inhibitor, enzyme/cofactor, receptor/hormone, receptor/effector, ligand/cell surface receptor, virus/ligand, etc. The term "binding partner," as used herein, refers to a molecule that can undergo binding with a particular molecule, forming a "binding pair." Thus, as an example, the detection entity may include a biotin moiety and the signaling entity may include an avidin or a streptavidin moiety that is determinable in some fashion, for example, by being coupled to a radioactive, a fluorescent moiety, an electron-dense moiety, etc. As another example, the signaling entity may be an antibody able to recognize the detection entity on the protein. The antibody may be labeled in some way, for example, radioactively, fluorescently, using an electron-dense moiety, etc.

In some embodiments, the detection entity may be added to the oxidized residue using an alkylating agent, for example, directly by reacting the oxidized residue directly with an alkylating agent, indirectly by reducing the oxidized residue and thereafter reacting the reduced residue with an alkylating agent, etc. As used herein, an "alkylating agent" is an agent able to alkylate a target reactant, i.e., the agent interacts with the target reactant such that an alkyl moiety is added to the target reactant (i.e., the compound becomes "alkylated"). In some cases, the alkylating agent itself may include the alkyl moiety that is transferred to the target reactant, e.g., the alkylating agent causes the formation of a covalent bond between the alkyl moiety and the target reactant. Typically, when the target reactant is a protein, the alkylating agent is able to react with the protein to cause alkylation of at least one moiety on the protein, in some cases without denaturing or otherwise damaging the protein. As one particular example, the alkylating agent may alkylate a thiol (—SH) moiety on a protein (e.g., from a cysteine residue) to form an alkylthio (—SR) moiety, where R is an alkyl moiety and "-" indicates attachment to the protein. It is to be noted that an alkylthio moiety does not include a disulfide (—SSR) moiety. As another example, the alkylating agent may alkylate a hydroxy (—OH) moiety on the protein (e.g., from a serine residue or threonine residue) to form an alkoxy (—OR) moiety. In some cases, in order to prevent or reduce signal interference with non-oxidized residues on the protein and/or from other, non-oxidized proteins, a blocking reaction is provided by the invention, where the non-oxidized residues are blocked or inhibited in some fashion, prior to the attachment of the detection entity on the oxidized residues.

As used herein, an "alkyl" moiety, attached to a residue, is a moiety containing at least one carbon atom that is covalently bound to the residue, and may include any number of carbon atoms, for example, between and 1 and 25 carbon atoms, between 1 and 20 carbon atoms, between 1 and 15 carbon atoms, between 1 and 10 carbon atoms, or between 1 and 5 carbon atoms. In some embodiments, the alkyl moiety will contain at least 1 carbon atom, at least 3 carbon atoms, at least 5 carbon atoms, or at least 10 carbon atoms; in other embodiments, the alkyl moiety will have at most 10 carbon atoms, at most 5 carbon atoms, or at most 3 carbon atoms. The alkyl moiety may be a non-cyclic or a cyclic moiety. The carbon atoms within the alkyl moiety may be arranged in any configuration within the alkyl moiety, for example, as a straight chain (i.e., a n-alkyl such as methyl, ethyl, propyl, butyl, pentyl, hexyl, heptyl, octyl, etc.), a branched chain, i.e., a chain where there is at least one carbon atom covalently bonded to at least three carbon atoms (e.g., a t-butyl moiety, an isoalkyl moiety such as an isopropyl moiety or an isobutyl moiety, etc.), a ring structure (e.g., cyclopropyl, cyclobutyl, cyclopentyl), etc. or any combination thereof. The alkyl moiety may contain only single bonds, or may contain one or more double and/or triple bonds within its structure, for example, as in an alkene, an alkyne, an alkadiene, an alkadiyne, an alkenyne, etc. In some cases, the alkyl moiety contains only carbon and hydrogen atoms; however, in other embodiments, the alkyl moiety may also contain one or more substituents, i.e., a non-carbon, non-hydrogen moiety may be present within the alkyl moiety, e.g., the alkyl moiety may be "heterogeneous," as in a heterocycloalkyl moiety. In certain embodiments, the alkyl moiety can include a halogen such as chlorine or bromine, an alkoxy moiety, an amine moiety, a carbonyl, a hydroxide, etc. If more than substituent is present within the alkyl moiety, then the substituents may each independently be the same or different.

In one set of embodiments, a nitrosylated protein is determined by reacting a nitrosothiol moiety on the protein to form an alkylthio moiety, for example, spatially determined (e.g., through visualization). In some cases, the alkylthio moiety may include a detection entity. An example of such a reaction is the initial reduction of a nitrosothiol moiety on the protein to a thiol moiety, followed by alkylation of the thiol moiety to form an alkylthio moiety. Any suitable reaction able to convert the nitrosothiol moiety on the protein to a thiol moiety may be used, for example, reduction of the nitrosothiol moiety. In one embodiment, the nitrosothiol moiety is reduced by exposing the protein to a reducing agent. A "reducing agent," as used herein, is given its ordinary meaning in the art, i.e., an agent that is able to cause a reactant to attain a more negative oxidation state. Examples of suitable reducing agents include, but are not limited to, an ascorbate (for example, sodium ascorbate or potassium ascorbate), dithiothreitol (DTT), glutathione (GSH), NADPH, NADH, beta-mercaptoethanol, tris-(2-carboxyethyl)phosphine, tris-(2-cyanoethyl)phosphine, etc.

The thiol moiety (—SH) may then be reacted to produce an alkylthio moiety (—SR), which may include a detection entity in some cases, for example, a binding partner such as biotin or avidin, a fluorescent moiety, a radioactive moiety, or the like. As an example, the thiol moiety may be exposed to an alkylating agent able to react with the thiol moiety to form an alkylthio moiety. For example, in one embodiment, the alkylating agent can include a maleimide moiety. In some cases, the maleimide may be covalently bonded to a detection entity, for example, a biotin moiety or a fluorescent moiety. As a specific non-limiting example, the alkylating agent may be N-(3-maleimidylpropionyl)biocytin (MBP) (or N-[6-(biotinamido)hexyl]-3-(2-pyridyldithio)propionamide), and/or a derivative thereof. As used herein, a "maleimide moiety" is a moiety having a general maleimide structure, e.g.:

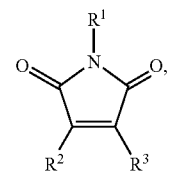

where each of $R^1$, $R^2$, and $R^3$ independently is a hydrogen atom (i.e., maleimide) or represents other, non-hydrogen atoms or group of atoms, for example, halogens, alkyls, alkoxyls, etc. In some cases, at least one of $R^1$, $R^2$, and $R^3$ may indicate attachment of the maleimide moiety to a fluorescent moiety, a biotin moiety (e.g., as in MBP), etc. Additionally, as used herein, a "biotin moiety" is a moiety having a general biotin structure, e.g.:

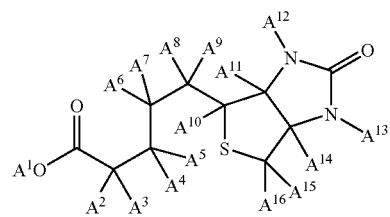

where each A in the above structure independently is a hydrogen atom (i.e., biotin) or represents other, non-hydrogen atoms or group of atoms, for example, halogens, alkyls, alkoxyls, etc. In some cases, at least one A in the above structure may indicate attachment of the biotin moiety to other moieties, for example, a fluorescent moiety.

In another embodiment, the alkylating agent includes an iodoacetamide moiety or an iodoacetate moiety, for example, as in 2-iodoacetamide or 2-iodoacetate, respectfully. In yet another embodiment, the alkylating agent includes at least one of p-chloromercuriphenylsulfonate, p-chloromercuribenzoate, dithiobis(2-nitro)benzoic acid, N-tosyllysyl chloromethyl ketone, 6-acryloyl-2-dimethylaminonaphthalene, dansyl aziridine, acrylodan, a benzylic halide, or a bromomethylketone. In some embodiments, more than one alkylating agent may be present, for example, N-ethylmaleimide and 2-iodoacetamide or 2-iodoacetate, etc.

In some cases, when other, unmodified thiol moieties are present within the protein and/or within other, proximate proteins near the protein suspected of being nitrosylated (or otherwise oxidized), the unmodified (i.e., non-nitrosylated) thiol moieties may be initially blocked or otherwise altered before the nitrosothiol moiety is converted into an alkylthio moiety, such that the unmodified thiol moieties are not able to react in the same fashion as the nitrosothiol moieties, which may confound the determination and analysis of the nitrosothiol moieties. In other cases, however, some side reactions involving other unmodified thiol moieties on the protein suspected of being nitrosylated and/or other, proximate proteins may be tolerable, as long as determination of nitrosylation within the protein can still be performed, for example, in in vitro assays, in protein studies, through visualization, or the like. Blocking or otherwise altering unmodified thiol moieties may be useful in some embodiments in isolating and/or boosting determination of any nitrosothiol moieties on the protein suspected of being nitrosylated, relative to unrelated, unmodified thiol moieties. Any suitable techniques for blocking unmodified thiol groups on a protein from reaction may be used. For example, thiol moieties on the protein may first be converted to alkylthio moieties (which typically will not contain detection entities), prior to reaction of the nitrosothiol moieties to form alkylthio moieties containing detection entities. As a non-limiting example, unmodified thiol moieties on a protein may be reacted with N-ethylmaleimide (NEM), methyl methanothiosulfonate, and/or derivatives thereof, prior to reaction/determination of nitrosothiol moieties in the protein, for example, using MBP.

In one set of embodiments, the detection entity can be directly determined, e.g., spatially, for example, through the use of fluorescence detection techniques such as spectroscopy, radioactivity, electron microscopy, etc. In other embodiments, however, the detection entity is indirectly determined, for example, through interaction of the detection entity with a signaling entity. For example, the signaling entity and the detection entity may together form a binding pair, e.g., as previously described. Typically, the signaling entity is externally determined, for example, using radioactivity, fluorescence, electron microscopy, etc. As a non-limiting example, if the detection entity comprises a biotin moiety, the signaling entity may include an avidin moiety, a streptavidin moiety, a biotin antibody, etc; the signaling entity may also include a fluorescent moiety, an enzymatic moiety, a radioactive atom, etc. Specific, non-limiting examples include streptavidin horseradish peroxidase (streptavidin-HRP), streptavidin fluorescein, or streptavidin fluorescein isothiocyanate (streptavidin-FITC).

The invention, in another aspect, may be used to determine a characteristic of a protein in vivo or in vitro. In one set of embodiments, a protein may be detected in vitro or in isolation, e.g., within a protein assay, for example, within a 96-well plate or other microwell plate. For instance, an embodiment of the invention may be used to determine oxidized proteins such as nitrosylated proteins in a sample, e.g., a synthetically prepared sample, a sample from cell culture or tissue culture, a cell lysate, and/or a sample from a subject, such as a human, a non-human primate, a cow, a horse, a pig, a sheep, a goat, a dog, a cat or a rodent such as a mouse, a rat, a hamster, a guinea pig, etc. A "sample," as used herein, is any cell, body tissue, or body fluid sample obtained from a subject. Examples of body fluids include lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

In another set of embodiments, oxidized proteins such as nitrosylated proteins may be determined in an intact cell. The intact cell may be alive, or the intact cell may be fixed in some cases. Determination of the protein in the cell may include determining the presence or absence of the proteins within the cell, determining the concentration of the proteins within the cell, and/or determining the location of the proteins within the cell, e.g., within organelles within the cell, such as within the nucleus, within mitochondria, within lysosomes, etc.

The invention, in yet another set of embodiments, provides for the determination of oxidized proteins such as nitrosylated proteins within tissue, for example, brain tissue, lung tissue, etc. In some embodiments, such determination of the nitrosylated and/or other oxidized proteins within the tissue allows the spatial locations and/or concentrations of the proteins within the tissues to be identified and/or measured, for example, quantitatively. The tissue may be alive, or fixed in some cases. Determination of the oxidized proteins may include determining the amount of protein present, and/or determining the spatial location of the oxidized proteins within the tissue, or within portions of the tissue (e.g., within certain structures comprising the tissue, within certain cells within the tissue, within certain regions of cells within the tissue, etc.). Thus, as a non-limiting example, a reaction where nitrosylated proteins become fluorescent may be used, according to the invention, to resolve the location of nitrosylated proteins within a tissue sample, such as within lung tissue. In still another set of embodiments, the invention provides for the determination of oxidized proteins, such as nitrosylated proteins, within a subject.

The oxidized protein (e.g., nitrosylated proteins), in some embodiments, may be spatially determined or resolved within a cell or tissue. For example, an oxidized protein may be determined to be within a cell and/or within a portion of the cell, such as within an organelle, for example, within the nucleus of the cell. In some cases, for instance, certain cells express nitrosylated proteins preferentially within the nucleus, e.g., as further described in the examples, below. In some instances, the concentration and the location of oxidized protein within the cell or tissue may both be determined. For instance, by using fluorescent and/or radioactive signals indicative of oxidized proteins, as previously described, the strength of the respective fluorescent and/or radioactive signal(s) may be correlated with the concentration of oxidized proteins, while the spatial location of the signal(s) may be correlated with the location of the oxidized proteins within the cell/or tissue.

Non-limiting examples of techniques that may be useful in determining oxidized proteins (for instance, oxidized proteins within a cell or a tissue that are reacted with a fluorescent detection entity, and/or a detection entity able to interact with a signaling entity that is or can become fluorescent upon interaction with the detection entity) include fluorescence detection techniques such as spectrofluorimetery, fluorescence microscopy, confocal microscopy, microwell plate readers, fluorescence photobleaching recovery techniques, fluorescence-activated cell sorting techniques, etc. Other techniques for determining fluorescence will be known to those of ordinary skill in the art. Thus, as non-limiting examples, a fluorescent detection entity or a fluorescent signaling entity may be detected in a protein solution, a cell lysate, a cell suspension, etc., using spectrofluorimetery techniques, microwell plate readers, or the like, while a fluorescent detection entity or a fluorescent signaling entity may be detected in live and/or intact cells or tissue using fluorescence microscopy, confocal microscopy techniques, etc. As another example, fluorescence-activated cell sorting techniques may be used to sort cells having or expressing a certain amount of oxidized proteins from cells that do not have or express those oxidized proteins.

Other examples of techniques that may be useful for determining oxidized proteins include radioactivity detection techniques such as scintillation counters, radioimmunoassay techniques, radiosensitive films, etc. Thus, in one example, cells or tissues containing oxidized proteins that are reacted with a radioactivity detection entity, and/or a detection entity able to interact with a radioactivity signaling entity, may be placed proximate radiosensitive film. The degree of radioactive exposure of the film may be indicative of the concentration of oxidized proteins within the cell or tissue, while the spatial location of the radioactive exposure may be indicative of the spatial distribution of oxidized proteins. Other suitable radioactivity detection techniques will be known to those of ordinary skill in the art.

Still other examples of techniques useful for determining oxidized proteins include detection techniques based on electron densities, for example, electron microscopy, such as TEM or SEM. As an example, a cell or a tissue containing oxidized proteins can be reacted with "heavy" or electron-dense moieties. As used herein, an "electron-dense moiety" is a moiety having an electron density determinably greater than the electron density of the atoms comprising the cell or tissue. Non-limiting examples of electron-dense moieties include gold, osmium, uranium, lead, platinum, chromium, palladium, etc., for example, present as individual atoms (e.g., in a chemical structure), as colloids or microspheres, or the like. A specific non-limiting example is MPB-labeled gold.

In one set of embodiments, binding of the detection entity to the protein is generally non-reversible, i.e., the detection entity may be bound to the protein under relatively benign conditions, but removal of the detection entity from the protein occurs under relatively harsh conditions, and in some cases, the detection entity cannot be removed from the protein without damaging and/or denaturing the protein. One non-limiting example method of determining reversibility is as follows. The detection entity is radiolabeled and reacted with the protein of interest. The unreacted label is removed, and the amount of radioactivity incorporated into the protein is determined, in the presence and in the absence of reducing agent. If the radiolabeled detection entity is reversibly attached, then the amount of radioactivity incorporated into the protein will be different for samples determined in the presence and in the absence of reducing agent; conversely, if the radiolabeled detection entity is non-reversibly attached, then the amount of radioactivity incorporated into the protein will be substantially the same in the presence and in the absence of the reducing agent. Other methods of determining reversibility include using fluorescence, electron-dense moieties, etc.

In yet another aspect, the present invention provides a kit suitable for determining nitrosylated proteins and other oxidized proteins, e.g., in vitro or in vivo, as previously described, optionally including instructions for use of the kit. The kit may include one or more of an alkylating agent, a detection entity, a reducing agent, a signaling entity, antibodies, instructions, suitable containers, or the like. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The kit may also include other components, depending on the specific application, for example, containers, cell media, salts, buffers, reagents, syringes, needles, etc.

In still another aspect, the invention includes the promotion of one or more of the above-described aspects. As used herein, "promoted" includes all methods of doing business, including methods of education, scientific inquiry, academic research, industry activity including pharmaceutical industry activity, and any advertising or other promotional activity including written, oral and electronic communication of any form, associated with the invention.

The following examples are intended to illustrate certain aspects of certain embodiments of the present invention, but do not exemplify the full scope of the invention.

EXAMPLE 1

This example describes certain protocols and methods that may be useful in various embodiments of the invention.

A line of spontaneously transformed mouse lung alveolar type II epithelial cells (C10) was used in some experiments, as described below. C10 cells were cultured in CMRL1066 medium containing 10% fetal bovine serum (FBS, GIBCO). In experiments involving microscopic analysis, the cells were grown on glass cover slips. At about one hour prior to exposure to a test agent, the medium was switched to phenol red free DMEM/F12 containing 0.5% FBS. Some cells were exposed to S-nitroso-glutathione (GSNO) or S-nitroso-N-acetyl penicillamine (SNAP) for about 1 hour, in the presence of an equimolar concentration of freshly prepared L-cysteine. To monitor S-nitrosylation in response to NOS2 activation, the cells were treated with 10 ng/ml TNF alpha (TNFα) and 100 U/ml interferon gamma (IFNγ), for about 24 hours. Incubation with L-N-monomethyl arginine (L-NMMA) for about 16 hours was used to inhibit endogenous NO production and D-NMMA (D-N-monomethyl arginine) was used as a control. Nuclear export was blocked by leptomycin B (5 ng/ml, exposure for about 12 hours). All experiments were performed in duplicate and were repeated at least three times.

S-nitrosothiols were detected in cell lysates or immunoprecipitated protein by chemiluminescence, using a nitric oxide analyzer (Ionics, Boulder, Colo.). Cell lysates were incubated for about 15 minutes in the presence or absence of sulfanilamide (0.5%). 50 microliters (12 micrograms of protein) of lysate were injected into a purge vessel containing 5 ml of 45 mM potassium iodide (KI) and 10 mM iodine ($I_2$) in glacial acetic acid, at 60° C., purged continuously with nitrogen.

Ran was immunoprecipitated from equivalent amounts of total cell lysates, using a Ran goat polyclonal IgG (Santa Cruz) and protein G-agarose beads. The immunoprecipitates were washed three times with HEN buffer (25 mM HEPES, pH 7.7, 0.1 mM EDTA, 0.01 mM neocuproine) and the immunocomplexes were injected into the purge vessel for NO analysis.

Biotin labeling of S-nitrosylated proteins in cell lysates proceeded as follows. At selected time points, cells were rinsed with PBS containing 0.1 mM EDTA and 0.01 mM neocuproine and lysed in HEN buffer containing 0.1% SDS, 0.5% CHAPS, and 20 mM NEM (N-ethylmaleimide) by rocking for 30 minutes at 4° C. The lysates were centrifuged at 14,000 g at 4° C. for about 10 minutes, and the excess NEM used to block sulfhydryl groups (SH) was removed by protein precipitation with acetone. The pellets were resuspended in HEN buffer containing 1% SDS (HENS), and the S-nitrosothiols were reduced and biotinylated by the simultaneous addition of 10 mM sodium ascorbate and 0.05 mM of the sulfhydryl-specific biotinylating agent, MPB (N-(3-maleimidylpropionyl) biocytin, Molecular Probes), for 1 hour at room temperature (RT, about 25° C.). Excess label was removed by a second acetone precipitation step, and the proteins were resuspended in HENS buffer for immunoprecipitation of RanGTPase, as described above. The immunoprecipitates were each washed three times with 500 microliters of HEN buffer, then resuspended in 25 microliters of HEN, followed by the addition of 25 microliters of 2× Laemmli sample buffer. The immunoprecipitates were then boiled at 95° C. for 5 minutes, separated by SDS-PAGE, and transferred to nitrocellulose membranes. Biotinylation of Ran was detected using streptavidin-HRP. Control experiments were also performed in which sodium ascorbate was omitted, preventing the reduction of S-nitrothiols. To assess the contribution of endogenous biotinylated proteins, MPB was omitted in some samples. All procedures prior to electrophoresis were carried out in the dark. Control dishes were subjected to mock manipulations and are referred to as sham controls.

To evaluate the localization of S-nitrosylated proteins in intact cells, the biotin derivatization method described above was used in combination with fluorophore labeling and visualized using confocal microscopy. Cells grown on cover slips were rinsed with PBS containing 0.1 mM EDTA and 0.01 mM neocuproine, and fixed in 4% PFA (paraformaldehyde) for 20 minutes at RT. The cells were permeabilized, and protein SH groups were blocked using HEN buffer containing 2.5% SDS, 0.5% CHAPS, and 20 mM MMTS (methylmethanethiosulfonate) for 20 min at 55° C. with constant shaking. After removal of MMTS, the cells were incubated with 1 mM sodium ascorbate and 0.4 mM biotin-HPDP (N-[6-(biotinamido)hexyl]-3'-(2'-pyridyldithio)propionamide) for about an hour at RT, and the cover slips were then incubated overnight with streptavidin-FITC at 4° C. Blocking was performed using 20 mM NEM for 30 minutes at 4° C., followed by incubation with 0.05 mM MPB and 1 mM sodium ascorbate for 1 hour at RT. The nuclei were stained with 10 microgram/ml PI (propidium iodide) for 30 minutes at RT. The cells were analyzed by confocal microscopy (magnification 40×) using an Olympus BX50 microscope coupled to a Bio-Rad (Hercules Calif.) MRC 1024 confocal scanning laser microscope system. Control experiments were also performed in which blocking of SH groups was omitted, or in which 100 micromolar $HgCl_2$ was added prior to blocking of SH groups with MMTS or NEM. To assess the contribution of endogenous biotinylated proteins, the biotin-label was omitted in some control cover slips. A diagram summarizing this procedure is shown in FIG. 1. All manipulations were performed in the dark.

In certain tissue experiments, Balb/c mice were anesthetized with 400 mg/kg Avertin (2,2,2-tribromoethanol) via intraperitoneal injection, and 50 microliters of 10 mM GSNO or PBS were administered intratracheally. Two hours later, the mice were euthanized by a lethal dose of pentobarbital via intraperitoneal injection. The lungs were instilled with PBS containing 0.1 mM EDTA and 0.01 mM neocuproine for about 10 minutes at a pressure of 25 $cmH_2O$, then put into a cassette, embedded in medium for frozen tissue specimens (OCT solution, Sakura Finetek, USA), and immediately frozen in isopentane cooled in liquid nitrogen for preparation of sections. Tissues were cut into 10 micrometer sections, affixed to glass microscope slides, and prepared for biotin derivatization. The tissue sections were washed in PBS containing 0.1 mM EDTA and 0.01 mM neocuproine, fixed in PFA (4%), for 20 minutes at RT, and permeabilized with PBS containing 1% Triton, 0.1 mM EDTA, 0.01 mM neocuproine, and 20 mM NEM for 30 minutes at 4° C. After removal of the solution, the sections were incubated with 1 mM sodium ascorbate and 0.05 mM MPB for about 1 hour at RT, then were incubated overnight with streptavidin-FITC at 4° C. The nuclei were stained with 10 microgram/ml PI for 30 min at RT, and the sections scanned using an Olympus BX50 upright microscope configured to a Bio-Rad MRX 1000 confocal scanning laser microscope system. Appropriate approval was granted from the institutional animal use committee.

EXAMPLE 2

This example demonstrates NO detection by chemiluminescence, using one embodiment of the invention. Using methods similar to those described in Example 1, this example demonstrates that the treatment of cells with exogenous S-nitrosothiols resulted in an increase in the SNO (nitrosothiol) content of the cells.

Mouse lung epithelial (C10) cells were incubated with 1 mM GSNO for about one hour, lysed, and the NO released following reduction in acidic $KI/I_2$ was detected by chemiluminescence. As shown in FIG. 2, the total NO content in lysates from cells treated with GSNO was found to have increased, as compared with lysates from non-treated cells. In order to eliminate the contribution of nitrites to the observed photoelectric signal, the cell lysates were incubated with a nitrite quencher, sulfanilamide, and assessed the sulfanilamide resistant NO signal by chemiluminescence. Under these experimental conditions, employing 12 micrograms of protein, S-nitrosthiol was not detected in the sham controls (<5 pmol), but a sulfamilamide-resistant NO signal was detected in lysates from cells treated with GSNO.

Figure 2A:
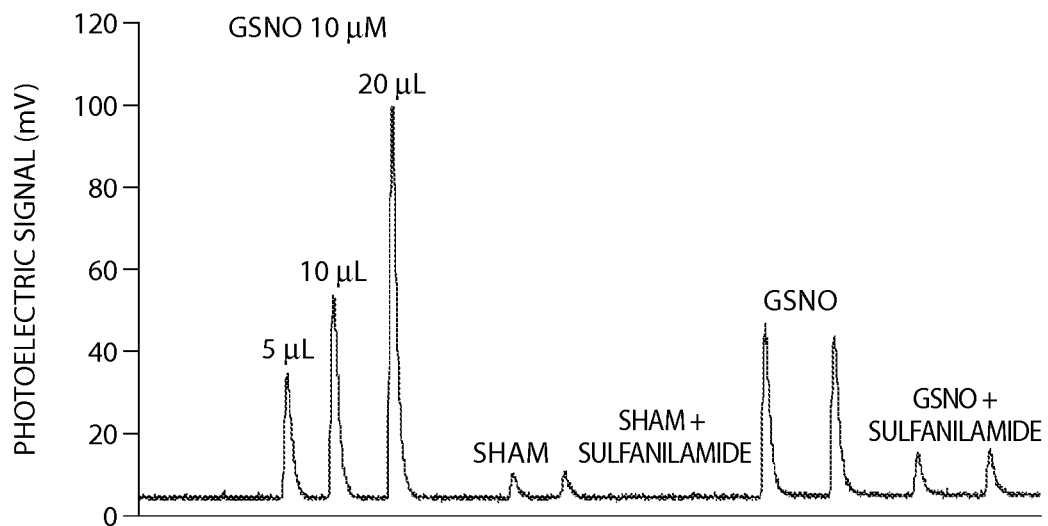
FIGS. 2A-2B are various graphs illustrating the nitrosothiol content of certain cell lysates following exposure of the lysates to S-nitroso-glutathione, according to another embodiment of the invention.
Figure 2B:
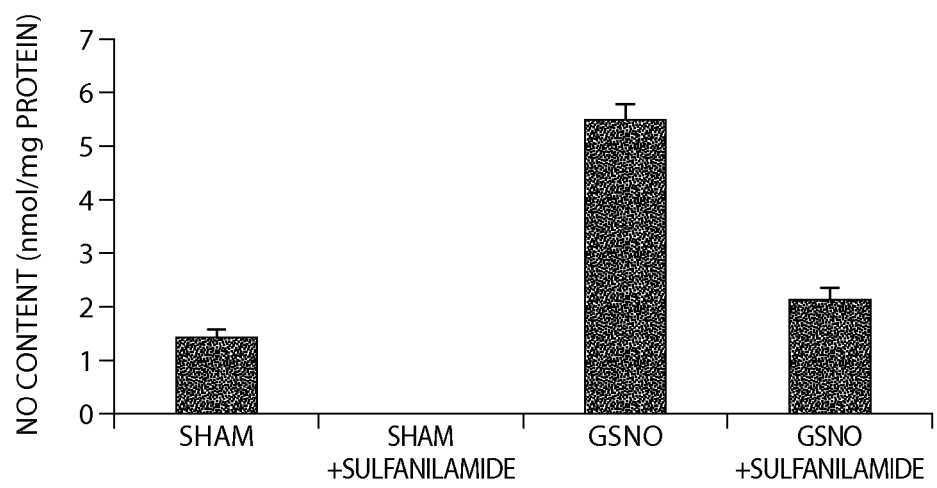

Sample data from these experiments are shown in FIG. 2. In FIG. 2A, the SNO content, determined using chemiluminecence detection, is plotted as a photoelectric signal (mV). FIG. 2B illustrates the detection of S-nitrosylated proteins using biotin derivatization, Western blotting and detection with streptavidin-HRP.

EXAMPLE 3

The detection of S-nitrosylated proteins in situ is demonstrated in this example, in accordance with an embodiment of the invention. Intact C10 cells were studied using methods similar to those described in Example 1. As shown in FIG. 3, S-nitrosylated proteins were detected in intact C10 cells using biotinylation, streptavidin-FITC and analysis by confocal laser scanning microscopy. C10 cells were exposed to 1 mM SNAP (FIG. 3C) or 1 mM GSNO (FIG. 3B) for about 1 hour, or to L-NMMA (FIG. 3D) or D-NMMA (FIG. 3E) for about 16 hours, fixed, and subjected to biotin derivatization, incubation with streptavidin-FITC, and confocal microscopy.

Figure 3A:
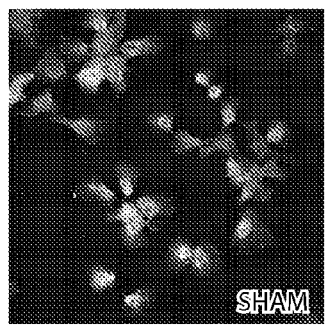
FIGS. 3A-3J are confocal laser scanning microscopy photomicrographs demonstrating the determination of S-nitrosylated proteins in intact cells, in accordance with another embodiment of the invention.
Figure 3B:
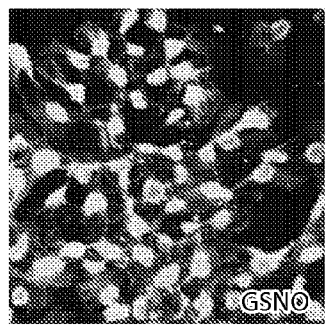
Figure 3C:
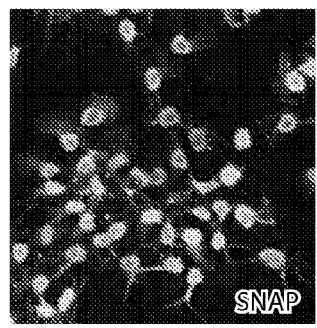
Figure 3D:
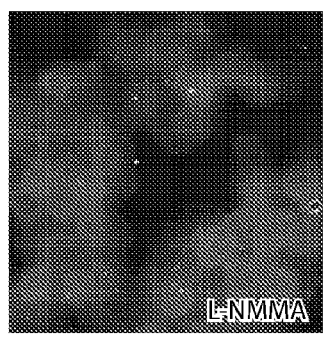
Figure 3E:
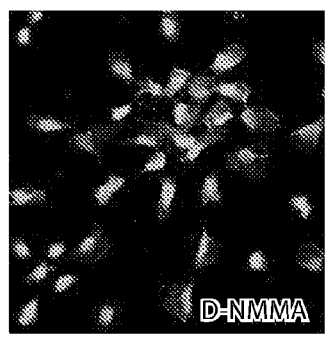
Figure 3F:
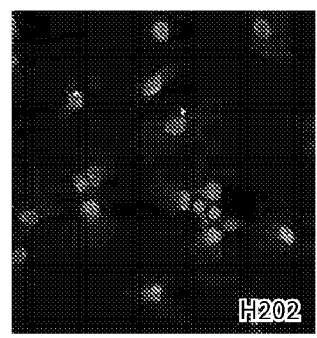
Figure 3G:
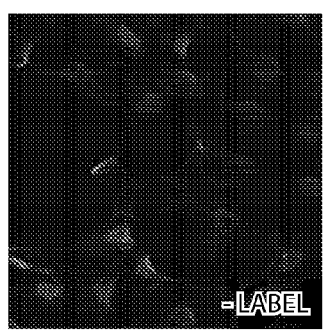
Figure 3H:
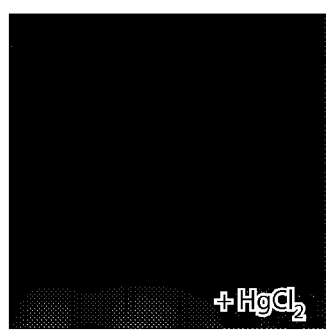
Figure 3I:
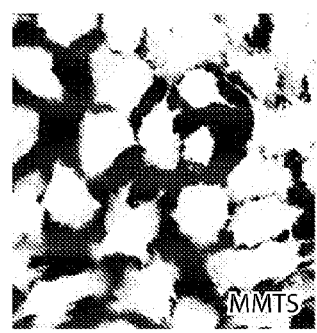
Figure 3J:
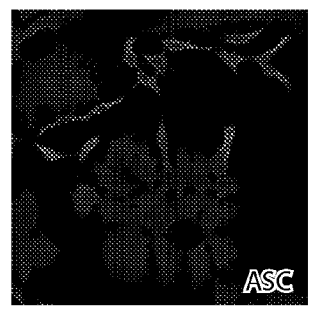

In non-treated cells (sham controls, FIG. 3A), some endogenous reactivity was observed. This reactivity was inhibited upon the addition of $HgCl_2$, which decomposes SNO prior to blocking with methyl methanethiosulfonate (MMTS) (FIG. 3H). The omission of ascorbate, which reduces SNO bonds prior to the addition of the biotin-HPDP label, also markedly decreased the observed reactivity (FIG. 3J). Furthermore, fluorescence was also not apparent when the biotin-HPDP label was omitted (FIG. 3G), indicating that the observed fluorescence was probably due to derivatization of S-nitrosylated proteins, and not endogenous biotin. In contrast, the omission of the SH blocking agent, MMTS, greatly enhanced biotinylation by biotin-HPDP, as a result of labeling of all available reduced cysteines (FIG. 3I). As an additional reagent control, the treatment of cells with 500 micromolar $H_2O_2$ for 15 minutes failed to alter the staining pattern, illustrating that cysteine oxidation per se does not promote biotinylation (FIG. 3F).

Similar to the data shown in FIG. 2, biotinylation was found to be enhanced in cells treated with GSNO or SNAP for 1 hour. Furthermore, treatment with L-NMMA substantially reduced biotinylation, whereas the inactive isomer D-NMMA did not affect the SNO pattern, thus demonstrating that the observed signals were dependent on endogenous NOS (nitric oxide synthase) activity and could be detected by the in situ method.

EXAMPLE 4

This example demonstrates that induction of NO production in C10 cells enhanced S-nitrosylation of proteins. C10 cells were stimulated simultaneously with tumor necrosis factor alpha (TNF α) and interferon gamma (IFN gamma or IFNγ) to induce NOS2 (Nitric oxide synthase, type 2) and elevate production of NO, which could then be detected in the medium as nitrites. Administration of these cytokines to the cells was found to cause nitrite accumulation in the medium over a 24 hour period, which was prevented with the addition of L-NMMA (1.1 micromolar). These results are shown in FIG. 4.

Figures 4A, 4B, 4C:
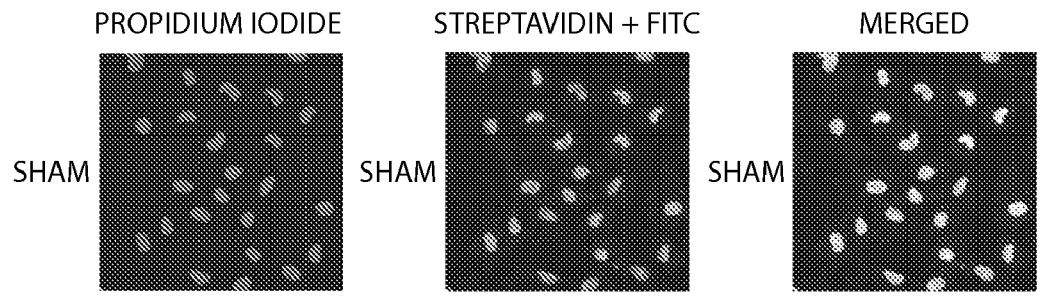
FIGS. 4A-4H are photomicrographs of cells demonstrating the determination of S-nitrosylated proteins following induction of the cells with NOS2, in accordance with another embodiment of the invention.
Figures 4D, 4E, 4F:
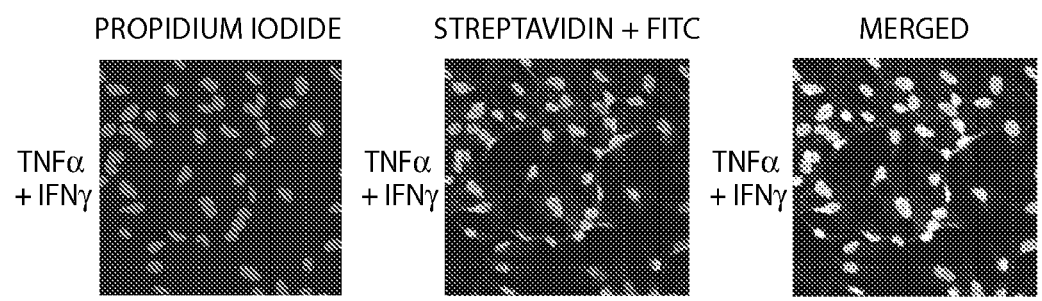

In FIGS. 4D-4F, the cells were stimulated with TNF alpha and IFN gamma for 24 hours (0.57 micromolar and 7.95 micromolar concentrations, respectively), fixed, and subjected to biotin derivatization and detection streptavidin-FITC via confocal laser scanning analysis as described above with respect to FIG. 3. Sham controls are shown for comparison in FIGS. 4A-4C. FIGS. 4A and 4D illustrate propidium iodide staining, FIGS. 4B and 4E illustrate streptavidin-FITC staining, and FIGS. 4C and 4F illustrate the superposition of propidium iodide staining and streptavidin-FITC staining. These figures demonstrate that the overall levels of S-nitrosylated proteins increased in cells stimulated with a combination of these cytokines, compared to sham controls, as determined by the enhanced streptavidin-FITC reactivity.

Figures 4G, 4H:
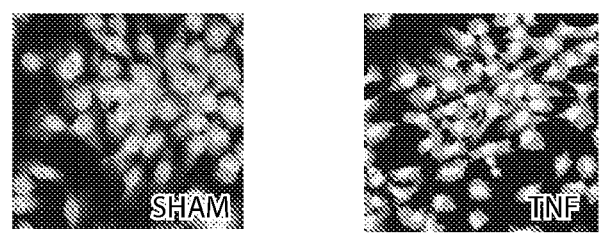

FIGS. 4G and 4H illustrates an assessment of the presence of cytoplasmic protein. C10 cells were mock-treated (sham) (FIG. 4G) or stimulated with TNF alpha for 30 minutes, and submitted to the biotinylation protocols similar to those described above with respect to FIG. 1. RelA (p65) was detected using specific antibodies (Santa Cruz). A marked cytoplasmic presence of RelA was found in sham cells and an enhanced nuclear presence in cells treated with TNF alpha, based upon dual staining with PI, indicating the presence of RelA within the nucleus (bright regions).

EXAMPLE 5

This example demonstrates the detection of S-nitrosylated proteins in frozen lung sections. In these experiments, mice were treated intratracheally with 50 microliters of 10 mM GSNO or PBS for about 2 hours, euthanized, and the lungs harvested and prepared for biotin derivatization, using methods similar to those described in Example 1. The biotinylated proteins were detected with streptavidin-FITC and the sections analyzed via confocal microscopy for tissue exposed to GSNO (FIG. 5B) or PBS (FIG. 5A). As controls, the MPB label was omitted, (-Label) (FIG. 5C) or $HgCl_2$ was used to specifically decompose S-nitrosothiols ($+HgCl_2$) (FIG. 5D).

As can be seen in FIG. 5, biotin reactivity, reflecting S-nitrosylated proteins, was apparent in lungs from PBS instilled animals and markedly increased in the lungs from animals treated with GSNO. The reactivity was found to have decreased when the sections were incubated with $HgCl_2$, to decompose the SNO, or when the biotin label was omitted.

EXAMPLE 6

In this example, the detection of S-nitrosylated proteins in cell nuclei was demonstrated. The reactivity of S-nitrosylated proteins detected by confocal microscopy in intact cells (FIGS. 3 and 4A) appeared to be largely confined, and suggested primarily localization within nuclei. To explore whether S-nitrosylation was localized within nuclei, in the experiments of this example, a propidium iodide (PI) as a nuclear stain to determine the extent of confinement of the S-nitrosylated proteins.

The merger of images obtained from dual staining with streptavidin-FITC (FIGS. 4B and 4E) and PI (FIGS. 4A and 4D), revealed significant co-localization in the nucleus (FIGS. 4C and 4F). Further, a Z-series taken throughout the cells confirmed that the streptavidin-FITC and PI signals were localized within the same plane of the cells (data not shown).

However, S-nitrosylation of target proteins may have occurred within the cytoplasm, prior to their translocation to the nucleus, and thus, the proteins may have accumulated within the nucleus. To show that the nucleus is indeed a site where S-nitrosylated proteins can accumulate, in this example, protein export from the nucleus was blocked using leptomycin B, which binds SH groups of CRM-1, a protein involved in nuclear export. The content and localization of S-nitrosylated proteins in the nucleus via biotin derivatization was then assessed, using methods similar to those described in Example 1.

Figure 6A:
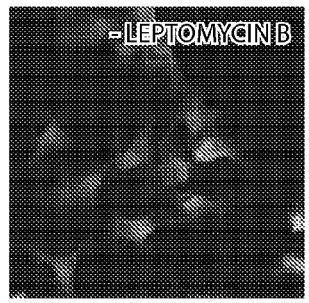
FIGS. 6A-6D are photomicrographs of cells illustrating increased content of S-nitrosylated proteins in the nucleus after exposing the cells to an agent that blocks nuclear export, in accordance with another embodiment of the invention.
Figure 6B:
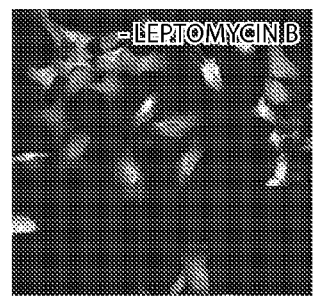
Figure 6C:
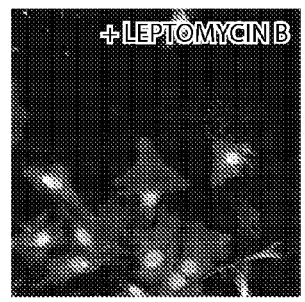
Figure 6D:
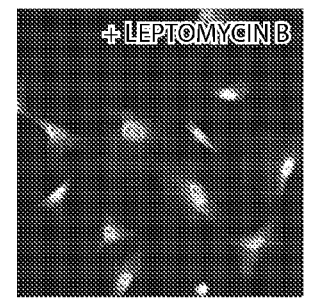

FIGS. 6A and 6C illustrate cells that were incubated with leptomycin B (5 ng/ml) for about 12 hours, followed by biotin derivatization, incubation with streptavidin-FITC, and analysis by confocal microscopy. As demonstrated in FIGS. 6A and 6C, leptomycin B enhanced biotinylation in the nuclear compartment. As a control, it was also demonstrated that the nuclear sequestration of RelA was enhanced by leptomycin B treatment, confirming that nuclear export was blocked (FIGS. 6B and 6D, showing immunostaining of RelA (p65)). These findings thus support the notion that S-nitrosylation occurs in proteins that are regulated by nuclear trafficking.

These findings suggested that the nucleus is an important site of localization of S-nitrosylated proteins. To ensure that the cytoplasmic targets were still present after this procedure, the presence of RelA was evaluated in sham or TNF alpha-treated cells. RelA, a subunit of the transcription factor, nuclear factor kappa B, is normally present in the cytoplasm and is translocated into the nucleus upon exposure to TNF alpha. These results, as shown in FIGS. 4G and 4H, demonstrated that in sham control cells, RelA was readily detected in the cytoplasmic compartment; however, in response to TNF alpha, increases in RelA in the nucleus were apparent, based upon co-localization with PI. These results thus suggested that the localization of S-nitrosylated proteins in the nucleus was not due to loss of cytoplasmic targets during the fixation and staining procedure. In fact, increased S-nitrosylation of cytoplasmic proteins was observed after induction of NOS2 activity.

The nuclear compartment may represent a micro-environment favorable for S-nitrosylation. Protein S-nitrosylation is readily reversible and the microenvironment that surrounds target proteins, such as pH, hydrophobicity, redox status, and the presence of transition metals, may be important regulating this post-translational modification. Also, the perinuclear region, where NOS has been localized, may be enriched with Golgi membranes, which may provide a hydrophobic environment which accelerates the reaction between NO and oxygen, forming $N_2O_3$ and consequently facilitating nitrosylation reactions. Thus, the perinuclear membranes may enhance the yield of S-nitrosylation, which may provide an example of a spatial environment that may be critical for the specificity of targeting NO reactions in some cases.

EXAMPLE 7

Example 6 demonstrated that S-nitrosylation may be present in the nucleus and may be enhanced after nuclear export is blocked. In this example, a potential target for S-nitrosylation was determined. RanGTPase is a 25 kDa protein containing 3 cysteine residues that is predominantly found in nuclear compartment in the cells, where it regulates nuclear import through the nuclear pore complex. In this example, it was investigated whether RanGTPase was S-nitrosylated after treatment of cells with GSNO.

Figure 7A:
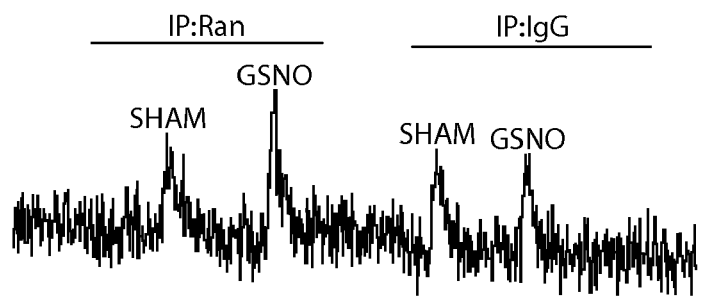
FIGS. 7A-7C illustrate the S-nitrosylation of RanGTPase, according to yet another embodiment of the invention.
Figure 7B:

Chemiluminescence was first performed to detect the S-nitrosylation of immunoprecipitated RanGTPase. Immunocomplexes from non-treated cells did not produce significant photoelectric signal, when compared to IgG controls. However, after GSNO treatment, an increase in the SNO content of immunoprecipitated RanGTPase was apparent, suggesting its S-nitrosylation (FIG. 7A). In these experiments, the cells were treated with 1 mM GSNO for about 1 hour, washed, and Ran was immunoprecipitated form the total lysate using a Ran-specific antibody and protein G agarose beads. The immunocomplexes were washed three times and directly injected into the purge vessel using techniques similar to those described in Example 1. As a control, pre-immune IgG was used instead of Ran antibody. Western blot analysis confirmed the presence of RanGTPase in the immunocomplexes (FIG. 7B).

Figure 7C:
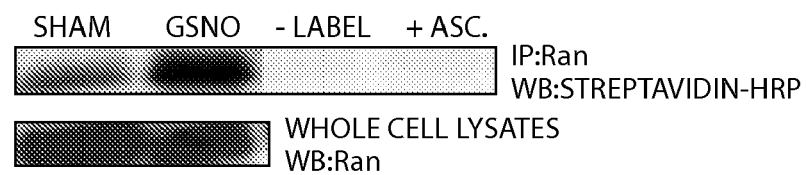

To confirm that RanGTPase itself was S-nitrosylated, a biotin derivatization approach was used, including immunoprecipitating RanGTPase and determining biotinylated RanGTPase by Western blotting using streptavidin-HRP. In these experiments, the cells were treated with GSNO, lysed, and subjected to biotin derivatization. Ran was immunoprecipitated from total cell lysates, and biotinylated RanGTPase was determined by Western blotting and by peroxidase-conjugated streptavidin (FIG. 7C, upper panel). In FIG. 7C, "-label" refers to the omission of the MPB label, and "-Asc" refers to the omission of ascorbate. In the lower panel of FIG. 7C, as a loading control, Ran was detected in whole cell lysates by Western blotting.

Some basal biotinylation of RanGTPase was observed, which was enhanced after treatment with GSNO. Minimal reactivity occurred in the absence of ascorbate or the biotin label (FIG. 7C, upper panel), suggesting that biotinylation was specific for SNO. It is of interest that RanGTPase is a target for S-nitrosylation. This protein has 3 cysteines, and is the most abundant member of the Ras superfamily of GTPases, constituting about 0.4% of the total cell protein.

EXAMPLE 8

In this example, the ability of ascorbate to significantly reduce GSSG (oxidized glutathione) to GSH (reduced glutathione) was investigated, under derivatization conditions similar to those described in the above examples. Various solution of GSSG were treated in HENS buffer with either 10 mM or 20 mM ascorbate ("asc"), then analyzed for its potential reduction to GSH by HLPC. As illustrated in Table 1, only a minor fraction of GSSG (less than 0.09%) was reduced under these conditions. Thus, the ascorbate-dependent SH biotinylation was believed to be primarily due to SNO, with only a minor contribution of disulfides.

TABLE 1

| GSSG µM | GSH µM | GSH µM 10 mM asc. | GSH µM 20 mM asc. | % GSSG reduced 10 mM asc. | % GSSG reduced 20 mM asc. |
| --- | --- | --- | --- | --- | --- |
| 100 | 0.10 µM | 0.11 µM | 0.11 µM | 0.01 | 0.01 |
| 500 | 0.57 µM | 0.96 µM | 1.29 µM | 0.08 | 0.14 |
| 1000 | 0.60 µM | 1.53 µM | 2.27 µM | 0.09 | 0.17 |

EXAMPLE 9

Nitric oxide (NO) possesses anti-inflammatory effects, which may be exerted via its ability to inhibit the transcription factor, Nuclear Factor kappa B (NF-κB). A commonly proposed mode of action for inhibition of NF-κB by NO involves interference with NF-κB binding to DNA. Since activation of inhibitory kappa B kinase (IKK), the prerequisite enzyme complex necessary to induce NF-κB, is subject to redox regulation, in this example, it was determined whether IKK could present a more proximal target for NO to inhibit NF-κB activation.

In this example, S-nitrosothiols (SNO) were shown to cause a dose-dependent inhibition of the enzymatic activity of IKK, in lung epithelial cells and in Jurkat T cells, which was associated with S-nitrosylation of the IKK complex. Using biotin derivatization of SNO, it was revealed that IKKβ, the catalytic subunit required for NF-κB activation, was a direct target for S-nitrosylation. A mutant version of IKKβ containing a cysteine 179 to alanine mutation was refractory to inhibition by SNO, or to increases in S-nitrosylation, in contrast to wild type IKKβ, demonstrating that cysteine 179 is the main target for attack by SNO. Importantly, inhibition of NOS activity in Jurkat T cells resulted in activation of IKK, in association with its denitrosylation. Moreover, NOS inhibition enhanced the ability of TNFα to activate IKK, illustrating the importance of endogenous NO in regulating the extent of NF-κB activation by cytokines. This example thus demonstrates that IKKβ is an important target for the redox regulation of NF-κB by endogenous or exogenous NO, providing an additional mechanism for its anti-inflammatory properties.

Nitric oxide (nitrogen monoxide, NO) is a pleiotropic short lived free radical that participates in diverse biological processes such as the regulation of vessel and airway tone, inflammation, neurotransmission and apoptosis. Although interactions with heme groups (such as in guanylyl cyclase) are the most recognized events associated with the signaling activities of NO, it is increasingly becoming appreciated that nitrosylation of protein sulfhydryl groups represents an important NO-dependent post-translational modification that impinges upon signal transduction cascades. Numerous proteins have been identified as targets for S-nitrosylation, including H-Ras, caspases c-Jun-N-terminal kinase (JNK), and ornithine decarboxylase. The inhibition of JNK by NO was recently described as a potential anti-inflammatory mechanism.

Nuclear factor kappa B (NF-κB) is a transcription factor that plays a pivotal role in inflammation, cell survival and proliferation. NF-κB is maintained in a latent form in the cytoplasm via sequestration by IκB inhibitory proteins. NF-κB activating stimuli cause the inducible degradation of IκB proteins, unmasking the nuclear localization signal of NF-κB, resulting in its nuclear translocation, binding to NF-κB motifs and the activation of gene transcription. The enzyme complex responsible for phosphorylation of IκB on specific serine residues is inhibitory kappa B kinase (IKK) which consists of at least 3 subunits: IKKα, IKKβ and IKKγ. Although IKKα and IKKβ are both catalytically active, studies in knock-out mice have demonstrated that IKKβ is responsible for degradation of IκB in response to many, but not all signals. In contrast, IKKα plays an important role in transcriptional activation of NF-κB responsive genes by phosphorylating histone H3. IKKγ is the regulatory subunit responsible for stabilizing the IKK complex and allowing interaction with upstream regulatory proteins.

Since the activation of IKK may be essential to induce NF-κB, IKK would also be an ideal target for negative regulation in order to prevent the activation of NF-κB. Arsenite, cyclopentenone prostaglandins, hydrogen peroxide, and 4-hydroxy-2-nonenal may be all capable of inhibiting IKKβ via targeting of cysteine residue(s) of IKKβ, resulting in a failure to activate NF-κB. Other studies have reported that NO is capable of modulating the activation of NF-κB. The inhibitory effect of NO on NF-κB is believed to play an important role in negative feed back regulation of NO production. The NOS2 gene promoter contains NF-κB regulatory sequences required for maximal gene activation and inhibition of NF-κB therefore decreases NOS2 gene activation, decreasing further production of NO. Multiple mechanisms have been described by which NO inhibits NF-κB. For instance, NO has been demonstrated to stabilize IκB, induce IκBα mRNA and prevent nuclear translocation of NF-κB. Recent emphasis has been focused on S-nitrosylation of cysteine 62 of the p50 subunit, which can inhibit the ability of NF-κB to bind DNA.

In this example, a line of spontaneously transformed mouse alveolar type II epithelial cells (C10) was propagated in CRML-1066 medium containing 50 U/ml penicilline-50 µg/ml streptomycin (P/S), 2 mM L-glutamine and 10% fetal bovine serum (FBS), all from GIBCO-BRL (Grand Island, N.Y.). Jurkat T cells were cultured in DMEM high glucose medium, supplemented with P/S and 10% FBS. At least 1 hour before adding the test agents, the cells were switched to phenol red-free DMEM/F12 containing P/S and 0.5% FBS, except for incubations with monomethyl-L-arginine (L-NMMA). Tumor necrosis factor (TNF) α, LNMMA, S-nitrosoglutathione (GSNO), S-nitroso-N-acetyl-D,L-penicillamine (SNAP) and S-nitrosocysteine antibody were purchased from Calbiochem (La Jolla, Calif.). The JNK1, IKKβ and γ, antibodies were purchased from Santa Cruz (Santa Cruz, Calif.), the IκBα antibody from Cell Signaling Technology (Beverly, Mo.), the phospho-IκBα antibody from BD Biosciences (Bedford, Mass.), the phosphoserine antibody from Zymed (San Fransisco, Calif.) and clasto lactacystin β-lactone from Sigma (St. Louis, Mo.). CSNO was prepared fresh prior to every experiment as described.

The cells were exposed to test agents and at indicated times, transferred to ice, washed twice with cold PBS, and lysed in buffer containing 50 mM HEPES, 150 mM NaCl, 1 mM EDTA, 2 mM $MgCl_2$, 10 mM $Na_3VO_4$, 1 mM phenylmethylsulfonyl fluoride, 0.1% Nonidet P-40, 10 µg/ml leupeptin, 1% aprotinin, 250 µM DTT and 100 µM NaF. The lysates were cleared by centrifugation at 14,000 rpm, 4° C. for 10 min. Protein concentrations were determined and the IKK complex was immunoprecipitated with an IKKγ antibody (Santa Cruz) at 4° C. for 1.5 h using protein G agarose beads. The precipitates were washed once with lysis buffer and twice with kinase buffer (20 mM HEPES, 20 mM β-glycerolphosphate, 1 mM $MnCl_2$, 5 mM $MgCl_2$, 2 mM NaF and 250 µM DTT). The kinase reaction was performed using 1 µg glutathione-S transferase (GST)-IκBα as a substrate, provided by Dr. Rosa Ten (Mayo Clinic, Rochester, Minn.), and 5 µCi $\gamma^{32}P$-adenosine triphosphate at 30° C. for 30 min. Kinase assays were performed in presence of 250 µM DTT, the minimal concentration necessary in order to maintain maximal TNFα-stimulated activity. The reactions were stopped by the addition of 2× Laemmli sample buffer. The samples were boiled and separated on 15% polyacrylamide gel, gels were dried and examined by autoradiography. In separate experiments, the immunoprecipitated IKK complex or JNK1 from TNFα-stimulated cells was exposed to SNAP or GSNO for 15 min in lysis buffer in vitro prior to assessment of kinase activity. The kinase reaction for JNK was performed using 1 µg GST-c-Jun as a substrate.

The C10 cells were transfected (Lipofectamine plus, Invitrogen, Carlsbad, Calif.) using 2 µg of plasmid (hemeagglutinin-tagged IKKβ wild type (wt HA-IKKβ) or HA-tagged IKKβ C179A, gifts of Dr. Michael Karin), for 3 hours, washed, and used in experiments 24 hours later. The transfection efficiency using this procedure approximates 30% (data not shown). No effects of empty vector were observed.

The detection of S-nitrosylated proteins was performed via a biotin switch method as follows. Following treatments, the cells were rinsed 2 times with PBS containing 0.1 mM EDTA and 0.01 mM neocuproine and lysed in HEN buffer (25 mM HEPES, pH 7.7, 0.1 mM EDTA, 0.01 mM neocuproine) containing 0.5% CHAPS, 0.1% SDS and 20 mM N-ethylmaleimide (NEM) at 4° C. for 30 min in order to block free thiols. The lysates were cleared by centrifugation at 14,000 g, 4° C. for 10 min and excess NEM was removed by protein precipitation using cold acetone. The protein pellets were resuspended in HENS buffer (HEN 1% SDS), and the SNO bonds were decomposed by adding 20 mM sodium ascorbate. The resulting free thiols were reacted with 0.05 mM sulfhydryl-specific biotinylating agent, N-(3-malemidylpropionyl) biocytin (MPB, Molecular Probes) for 30 min at room temperature, resulting in biotinylation of SNO. Following the removal of excess MPB by another protein precipitation using acetone, IKK was immunoprecipitated using IKKβ or HA (12CA5, Roche, Indianapolis, Ind.) antibodies. The immunoprecipitates were washed 3 times with HEN buffer and resuspended in 50 µl HEN containing Laemmli sample buffer, boiled at 95° C. for 5 min, loaded on 10% acrylamide gels and transferred to nitrocellulose. Biotinylated IKKβ was detected on the membrane using horseradish peroxidase-linked streptavidin. To confirm equal amounts of IKKβ, biotinylated lysates were also subjected to Western blotting for IKKβ or HA. To confirm the specificity of SNO labeling, addition of MPB or reduction by ascorbate was omitted in some samples. All procedures until biotinylation were performed in the dark.

A fraction of the lysates used for in vitro kinase assays, biotin derivatization or chemiluminescence was mixed with 2× Laemmli sample buffer, samples were boiled and loaded on a 10% polyacrylamide gel. The proteins were transferred to nitrocellulose and membranes blocked in 5% milk in Tris-buffered saline (TBS). After 2 washes in TBS containing 0.05% tween-20 (TBS-Tween), the membranes were incubated with primary antibodies against HA, IKKγ, IKKβ, JNK1, IκBα, phospho-IκBα or phosphoserine for 1 h at RT. The membranes were washed 3 times 20 min in TBS-Tween, and incubated with a peroxidase-conjugated secondary antibody for 1 h at RT. After three 15 min washes with TBS-Tween, conjugated peroxidase was detected by chemiluminescence according to the manufacturer's instructions (Kirkegaard and Perry Laboratories, Gaithersburg, Md.).

The total cellular SNO concentration (protein-bound plus free) was measured in lysates of cells treated with SNO in presence or absence of L-or D-cys. After 3 washes with PBS, the cells were lysed in the same buffer as was used for the biotin switch method. The nitrate was quenched with 0.6% sulfanilamide in 1M HCl for 10 min at RT, and the samples were injected into 5 ml of a solution of 45 mM KI and 10 mM $I_2$ in glacial acetic acid at 60° C., contained within a purge vessel, and connected to a NO chemiluminescence analyzer (Ionics, Boulder, Colo.). The amount of NO released from samples was estimated from a standard curve generated by injection of L-CSNO stock solutions. IKKβ was immunoprecipitated from Jurkat T cell lysates, using a monoclonal IKKβ antibody and protein G-agarose beads. After washing the immunoprecipitates 3 times with HEN buffer containing 50 mM NaCl to minimize co-associating proteins, the antigen-antibody complexes were removed from the beads by three 10 min incubations in 50 μl of 100 mM glycine pH 3.0 at 4° C. The eluates were treated with 0.6% sulfanilamide prior to the assessment of the SNO content via chemiluminescence, as described before. As a control, some lysates or immunoprecipitates were treated with 4.4 mM $HgCl_2$ for 10 min at RT, followed by 20 min incubation at 4° C., and 10 min incubation with sulfanilamide at RT. To confirm that IKKβ was the predominant protein immunoprecipitated under these conditions, Laemmli sample buffer was added to the immunoprecipitate, samples were boiled, and evaluated on a silver-stained gel. All experiments were repeated at least two times and similar results were obtained.

Figure 8A:
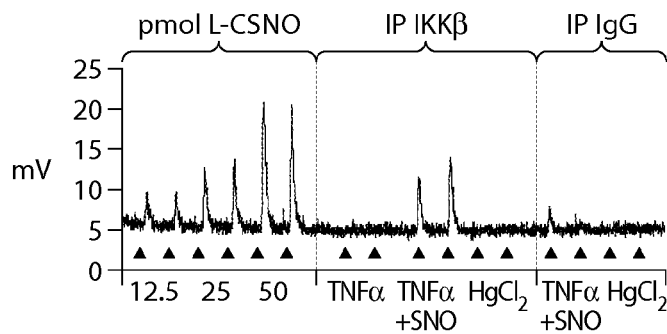
FIGS. 8A-8C illustrate the S-nitrosylation of subunit beta of inhibitory kappa B kinase (IKKβ), according to one embodiment of the invention.
Figure 8B:
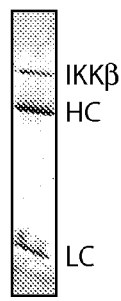

Since the kinase activity of the β subunit of the IKK complex was found to be responsible for phosphorylation of IκBα in response to TNFα, and this was inhibited upon treatment with SNO, it was assessed whether IKKβ represents a direct target for S-nitrosylation. For this purpose IKKβ was immunopurified from TNFα-stimulated Jurkat T cells treated with SNO, and chemiluminescence analysis was performed to determine the SNO content of IKKβ. While a SNO signal was not detected from IKKβ immunopurified from lysates of untreated cells (data not shown) or cells stimulated with TNFα (FIG. 8A), IKKβ obtained from cells exposed to L-CSNO and TNFα demonstrated a marked increase in SNO content. The observed chemiluminescence signal was not due to contaminating nitrite since the samples were treated with sulfanilamide to quench nitrite. In addition, the chemiluminescence signal was completely ablated following $HgCl_2$ treatment, indicating that the measured NO was derived from SNO within the immunopurified protein. Control immunoprecipitations with equal amounts of an isotype-matched control antibody resulted in a barely detectable signal. Analysis of the immunoprecipitate by silver staining (FIG. 8B) revealed that IKKβ was the major detectable protein under the conditions used here, confirming that the measured NO was likely derived from SNO bonds in IKKβ and not from other co-immunoprecipitated proteins.

Figure 8C:
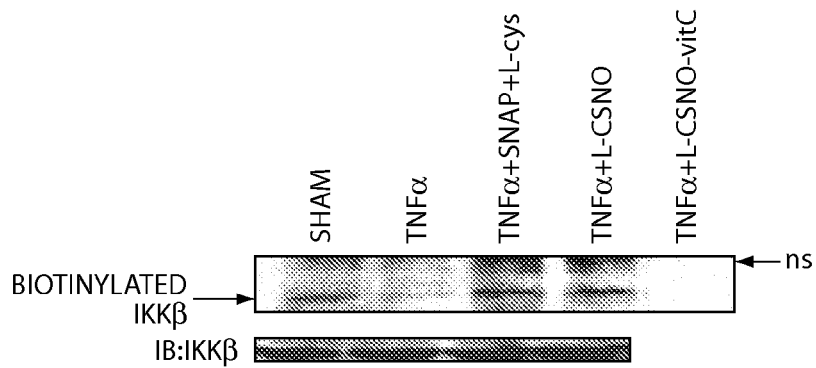

A biotin derivatization method was also used to assess whether the IKKβ subunit is directly targeted by S-nitrosylation. For this purpose, Jurkat T cells were treated as described before, and cell lysates were derivatized in order to selectively biotinylate SNO moieties. IKKβ was subsequently immunoprecipitated from the lysates and its biotinylation was assessed using streptavidin-HRP on a western blot. The results in FIG. 8C demonstrate detectable endogenous S-nitrosylation of IKKβ in untreated cells, which was decreased in response to TNFα. Furthermore, SNAP/L-cys or L-CSNO caused an increase in S-nitrosylation of IKKβ. Biotin labeling was absent when ascorbate was omitted in the derivatization procedure, showing the specificity of biotinylation for detection of SNO.

Figure 9A:
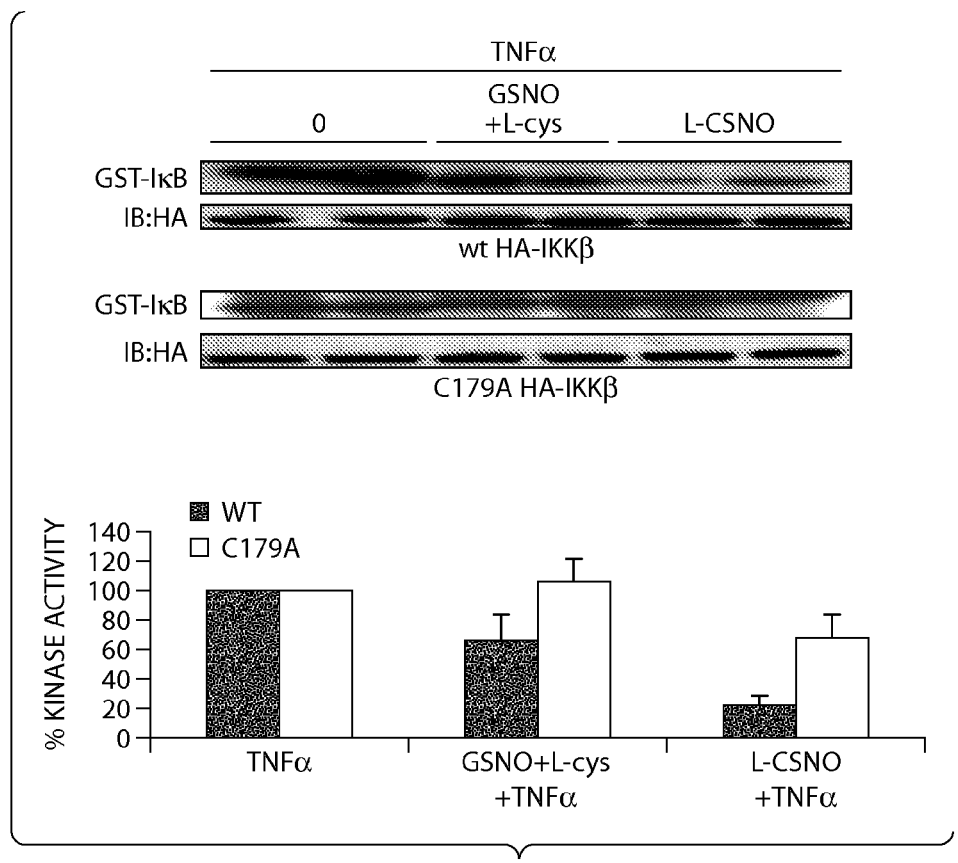
FIGS. 9A-9B illustrate that cysteine-179 of IKKβ is target for S-nitrosylation, in accordance with an embodiment of the invention.
Figure 9B:
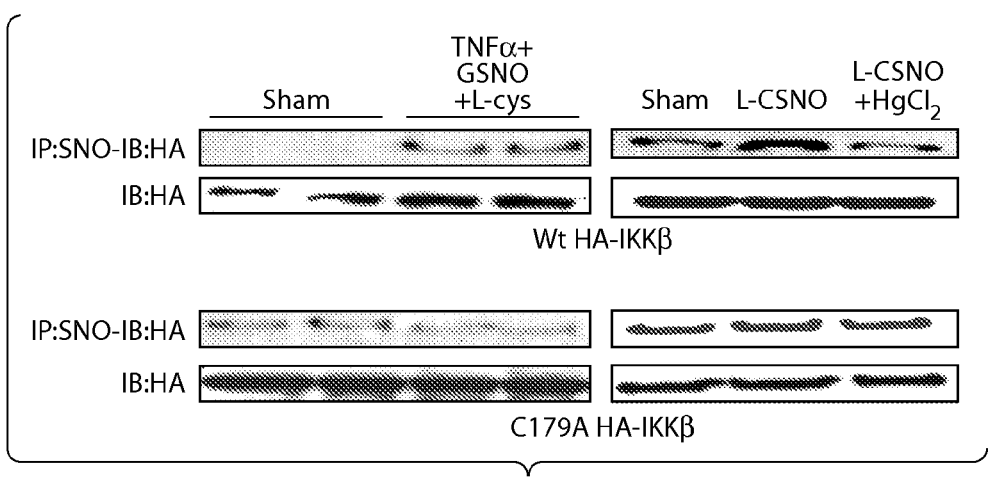

Cys 179 is located in between serines 177 and 181, which are required for activation of IKKβ by TNFα. Since it has been shown that cys 179 is a target for inhibition by arsenite, it was investigated if this residue was specifically targeted by S-nitrosylation. For this purpose, wt HA-IKKβ or cys179 to ala mutated HA-tagged IKKβ (C179A HA-IKKβ) were transfected into C10 cells, which were then treated with SNO to assess the extent of inhibition of TNFα-stimulated enzymatic activity. As is apparent from FIG. 9A, both GSNO/L-cys as well as L-CSNO inhibited the activity of wt HA-IKKβ. In contrast, C179A HA-IKKβ was largely refractory to inhibition by SNO. Accordingly, the treatment of cells with GSNO/L-cys increased S-nitrosylation of wt HA-IKKβ, but not of C179A HA-IKKβ as revealed by immunoprecipitation using an antibody directed against SNO and western blotting for HA (FIG. 9B, left panels). The selectivity of the SNO antibody was demonstrated by incubating lysates of L-CSNO treated cells with $HgCl_2$, prior to immunoprecipitation with the SNO antibody, which resulted in a markedly lower amount of wt HA-IKKβ recovered by immunoprecipitation (FIG. 9B, right panel, top) whereas $HgCl_2$ did not affect the amount of C179A HA-IKKβ immunoprecipitated with SNO antibody (FIG. 9B, right panel, bottom), illustrating some non-specific reactivity of this antibody. Collectively, these data demonstrate that cysteine 179 of IKKβ is a major target for S-nitrosylation and inhibition by SNO.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

As used herein, "or" should be understood to mean inclusively or, i.e., the inclusion of at least one, but including more than one, of a number or list of elements. Only terms clearly indicated to the contrary, such as "only one of" or "exactly one of," will refer to the inclusion of exactly one element of a number or list of elements.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements that the phrase "at least one" refers to, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one act, the order of the acts of the method is not necessarily limited to the order in which the acts of the method are recited.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for determining protein nitrosylation, the method comprising:
   transporting an alkylating agent comprising a detection entity to intact cells;
   reacting a first thiol moiety on a protein in the intact cells to form an alkylthio moiety and block the first thiol moiety from being labeled by subsequent reaction with the detection entity;
   reacting a nitrosothiol moiety on the protein using an ascorbate to form a second thiol moiety; and
   reacting the second thiol moiety with the alkylating agent comprising the detection entity to form a second alkylthio moiety to spatially determine protein nitrosylation within the intact cells, wherein the first thiol moiety is substantially blocked from reaction with the detection entity.

2. The method of claim 1, wherein the protein is in a tissue.

3. The method of claim 2, comprising visually determining the protein within the tissue to determine protein nitrosylation.

4. The method of claim 1, comprising detecting a fluorescent signal associated with the protein nitrosylation.

5. The method of claim 1, wherein the act of transporting an alkylating agent comprises permeabilizing the cells to transport therein the alkylating agent.

6. A method for determining protein nitrosylation, the method comprising:
   transporting an alkylating agent and an ascorbate to intact cells;
   reacting a first thiol moiety on a protein with the alkylating agent in the intact cells to form an alkylthio moiety;
   reacting a nitrosothiol moiety on the protein with the ascorbate to form a second thiol moiety; and
   spatially determining the second thiol moiety in the intact cellsby reacting the second thiol moiety with an alkylating agent comprising a detection entity to form a second alkylthio moiety.

7. The method of claim 6, wherein the act of transporting the alkylating agent and the ascorbate comprises permeabilizing the intact cells to transport therein the alkylating agent and the ascorbate.

8. The method of claim 6, wherein the intact cells form a tissue.

* * * * *

UNITED STATES PATENT AND TRADEMARK OFFICE
CERTIFICATE OF CORRECTION

PATENT NO.        : 8,053,243 B2                         Page 1 of 1
APPLICATION NO.   : 11/104387
DATED             : November 8, 2011
INVENTOR(S)       : Yvonne M. Janssen et al.

It is certified that error appears in the above-identified patent and that said Letters Patent is hereby corrected as shown below:

In the Claims
At column 22, claim 6, line 38, please change "cellsby" to --cells by--.

Signed and Sealed this
Twentieth Day of December, 2011

David J. Kappos
Director of the United States Patent and Trademark Office